United States Patent [19]

Chromecek et al.

[11] 4,436,887
[45] Mar. 13, 1984

[54] N-VINYL LACTAM BASED BIOMEDICAL DEVICES

[75] Inventors: Richard C. Chromecek, Macedon; Gary D. Friends, Ontario; Lawrence Y. Wissman; Raymond A. Yourd, III, both of Rochester, all of N.Y.

[73] Assignee: Bausch & Lomb Incorporated, Rochester, N.Y.

[21] Appl. No.: 320,355

[22] Filed: Nov. 12, 1981

[51] Int. Cl.$^3$ ............... C08F 226/06; C08F 226/08; G03B 21/46

[52] U.S. Cl. ............... 526/263; 351/160 R; 351/160 H; 523/108; 526/259; 526/260; 526/262; 526/264; 528/499; 528/500

[58] Field of Search ............ 526/259, 260, 263, 262, 526/264; 528/499, 500; 351/160 R, 160 H

[56] References Cited

U.S. PATENT DOCUMENTS

| | | | |
|---|---|---|---|
| 2,541,152 | 2/1951 | Cairns | 526/263 |
| 3,532,679 | 10/1970 | Steckler | 260/80.72 |
| 3,759,880 | 9/1973 | Hoffmann et al. | 260/80.3 |
| 3,772,235 | 11/1973 | Stamberger | 260/29.6 |
| 3,787,380 | 1/1974 | Stamberger | 260/80.7 |
| 3,949,021 | 4/1976 | Kunitomo et al. | 260/895 |
| 3,992,562 | 11/1976 | Denzinger et al. | 260/47 UA |
| 4,013,825 | 3/1977 | Denzinger et al. | 260/47 UA |
| 4,022,754 | 5/1977 | Howes et al. | 260/47 UA |
| 4,036,814 | 7/1977 | Howes et al. | 260/47 UA |
| 4,158,089 | 6/1979 | Loshaek et al. | 526/264 |
| 4,182,802 | 1/1980 | Loshaek et al. | 526/264 |
| 4,184,992 | 1/1980 | Hosaka | 260/29.7 |

FOREIGN PATENT DOCUMENTS 1511716 5/1978 United Kingdom .

OTHER PUBLICATIONS

J. Pol. Sci., Pt A-1, vol. 7, 35-46 (1969).

*Primary Examiner*—Harry Wong, Jr.
*Attorney, Agent, or Firm*—Robert M. Phipps; B. D. Bogdon

[57] ABSTRACT

N-vinyl lactam monomers and comonomers are cross-linked with resonance free di(alkene tertiary amine) cyclic compounds to obtain biomedical devices, including contact lenses, which have high oxygen permeability and good mechanical properties.

27 Claims, No Drawings

N-VINYL LACTAM BASED BIOMEDICAL DEVICES

BACKGROUND OF THE INVENTION

1. Field of the Invention

This invention relates to soft, high water content, biomedical devices including contact lenses prepared from N-vinyl lactam monomers with or without comonomers and crosslinked with a resonance free di(alkene tertiary amine) cyclic compound.

2. Prior Art Statement

Many attempts have been undertaken to resolve the problem of polymerization and copolymerization of N-vinyl lactams with the methacrylate type comonomers. An important characteristic of the resulting polymers is their ability to absorb water and it has been a goal to obtain polymers with high water absorption characteristics while not sacrificing other properties. To date, these polymers with a water content of about 60% or more have been found to be mechanically weak and exhibit high percentages of extractibles after polymerization.

U.S. Pat. No. 3,532,679 (Steckler) describes the polymerization of N-vinyl lactams with alkyl methacrylates such as methyl, ethyl, butyl, 2-hydroxy ethyl, in the presence of a crosslinking agent which is preferably tetraethyleneglycol dimethacrylate. The resulting polymers have water absorption contents of 52% to 95%, however, they can be extracted very easily and lose their original high water content. This reversal of properties is caused by the failure of the dimethacrylates to uniformly copolymerize with the N-vinyl lactam. The hydrogel polymers of this patent are disclosed as suitable for dentistry, surgery, ophthalmology and similar applications.

U.S. Pat. No. 4,022,754 (Howes et al) discloses a copolymer of 3-methoxy-2-hydroxypropyl methacrylate (G-MEMA) and N-vinyl lactams crosslinked by a class of di- or multi-functional monomers such as allyl methacrylate or 3-allyloxy-2-hydroxypropyl methacrylate to improve the mechanical strength of the polymer. The copolymers are disclosed as being useful as contact lenses. However, the water content of these copolymers remains low, around 55%. Subsequently, U.S. Pat. No. 4,036,814 (Howes et al) discloses that when the N-vinyl lactam monomer is copolymerized with an aryl or an aryloxy acrylate, or methacrylate or the corresponding amide, a water content of 80% with retention of reasonable mechanical properties can be achieved. The disclosed copolymers include benzyl methacrylate and phenoxyethyl methacrylate. The previously disclosed crosslinking agents are also employed with the new comonomer. Unfortunately, no oxygen permeability data for these polymers is disclosed.

U.S. Pat. No. 3,772,235 (Stamberger) discloses using glycidyl methacrylate, glycidyl acrylate or glycidyl crotonate as the crosslinking agent for a hetrocyclic N-vinyl monomer such as N-vinyl pyrrolidinone to obtain transparent hydrogels suitable for optical lenses. The polymers thus prepared have water contents ranging from 30% to 70%. Stamberger further discloses in U.S. Pat. No. 3,787,380 the addition of a second comonomer such as methyl methacrylate to obtain a water absorption of 60% to 83%. The polymers are stated to be machinable but no mechanical or oxygen permeability data is presented.

U.S. Pat. No. 3,759,880 (Hoffmann et al) discloses the preparation of poly-N-vinyl pyrrolidinone-2 by polymerizing vinyl pyrrolidinone in the presence of 0.5 to 10 weight percent of a cyclic acid amide containing at least two ethylenically unsaturated groups and an oxidizable metal. Suitable acid amides include N,N'-divinyl ethylene urea and N,N'-divinyl propylene urea. The resulting insoluble and only slightly swellable polymers are useful for clarifying beer, wine and fruit juices.

U.S. Pat. No. 3,992,562 (Denzinger et al) and U.S. Pat. No. 4,013,825 (Denzinger et al) disclose variations of the above Hoffmann et al process in which selected sulfur compounds or ketocarboxycyclic acids or esters are respectively substituted for the oxidizable metal. Another patent to the same assignee, U.K. Pat. No. 1,511,716, discloses the use of similar polymers and copolymers in the field of coatings where divinyl ethylene urea provided better abrasion resistance. None of the examples in these four patents shows the possibility of fabricating an optically clear polymer suitable for contact less manufacturing nor suggests properties associated with polymers used in such an application.

U.S. Pat. No. 3,949,021 (Kunitomo et al) discloses improving the weak mechanical properties of N-vinyl pyrrolidinone or a combination of N-vinyl pyrrolidinone and other vinyl monomers by simultaneously polymerizing and crosslinking in the presence of soluble linear-polymers such as poly(methyl methacrylate) and monomers such as diallyl phthalate, ethylene glycol diacrylate, hexamethylene bismaleimide, divinyl benzene and divinyl urea. The crosslinking agents having allyl groups are preferred. The resulting polymers have a water absorption of 60% to 90% and are useful for contact lens purposes. Divinyl urea is mentioned among the crosslinking agents, however, it was found that this compound does not polymerize efficiently as suggested by this patent.

Polymerization of N,N'-divinyl urea was studied by C. G. Overberger et al, J. Pol. Sci., Pt A-1, vol. 7, 35–46 (1969). It was found that although the divinyl urea exists at room temperature in its vinyl form, the tautomeric form (1)—CO—N=CH—CH$_3$, is formed upon heating. The resulting polymer has the structure

Thermal polymerization of divinyl urea results in soluble (non-crosslinked) polymers. Photo-initiated polymerization of divinyl urea gave similar products. Finally, radical-initiated polymerization of divinyl urea resulted in insoluble material in lower yield. However, the infrared spectrum and elemental analysis showed all three products to be identical.

U.S. Pat. No. 4,184,992 (Hosaka) summarizes the disadvantages of the prior art N-vinyl lactam base polymers for contact lenses. It was found that those previous art polymers became opaque, distorted upon immersing in boiling water and contained water-soluble extractibles. Hosaka's object was to provide a crosslinking agent reactive with the rest of the monomers to produce a hydrogel having a minimum extractibles and no change in boiling water. The object is more nearly achieved by the use of crosslinking agents with a vinyl or allyl functionality (similar in concept to U.S. Pat. No. 4,036,814) such as vinyl methacrylate, divinyl succinate, triallyl isocyanurate. In the case of polymers having water contents of 68% to 70% the amount of extractibles after 16 hours immersion in boiling water was diminished to between 5% and 10%. In the case of polymers having a water content of 73%, the comparable result was 7% to 9%.

U.S. Pat. No. 4,158,089 (Loshaek et al) introduces allylic monomers such as mono and diallyl itaconate, diallyl maleate, diallyl fummarate as crosslinking agents for N-vinyl pyrrolidinone/alkyl acrylate or methacrylate polymers and compares the properties of these polymers with poly(hydroxyethyl methacrylate) commercially available under the tradename Dura-Soft. Depending on the amount of crosslinking agent, diallyl itaconate, the polymers exhibit water content between 60% and 98% with extractibles of 9% to 20%. The polymer's mechanical strength rating is much inferior to poly(hydroxyethyl methacrylate) which is rated 10, a polymer with a strength rating of 5 has a 57% water content, a polymer with a strength rating of 3 has a 71% water content and a polymer having a strength rating of 3 to 4 has an 80% water content. To achieve low extractibles, 10% or lower at high water content, usually high amounts of crosslinking agent is necessary. The high amount of crosslinking agent causes the formation of rigid polymers having low strength rating. U.S. Pat. No. 4,182,802 (Loshaek et al) discloses a further attempt to improve the property of this type of polymer by the incorporation of styrene as a comonomer. Again, as long as the amount of crosslinking agent is low, higher extractibles, 10% to 18% resulted.

From the foregoing, it can be appreciated that there is still a need for an optically clear polymer of N-vinyl lactam which has low extractibles, good mechanical properties (especially the tear strength), high oxygen permeability and good machinability for use in various biomedical applications.

SUMMARY OF THE INVENTION

In accordance with this invention, N-vinyl lactam crosslinked polymer or copolymer for biomedical applications characterized by oxygen permeability and high water absorption is improved by the use of a resonance free di-(alkene tertiary amine) cyclic compound as the crosslinking agent of said polymer or copolymer whereby improved tear strength, good machinability, low extractibles and high oxygen permeability are obtained. The obtained polymers and copolymers are clear and suitable for biomedical applications, including extended wear contact lenses, heart valves and films. More particularly, the invention concerns soft contact lenses for extended wear purposes.

DESCRIPTION OF THE PREFERRED EMBODIMENTS

The monomers employed in accordance with this invention are readily polymerized to form 3-dimensional polymeric networks which permit the transport of oxygen and are optically clear, strong and soft. The term "soft" is used in the well established sense of the contact lens field to describe polymeric products which are either flexible or semiflexible.

The nitrogen containing monomer used in the preparation of the polymers and copolymers of this invention is conveniently referred to as an N-vinyl lactam which includes (a) N-vinyl lactams per se and (b) other heterocyclic N-vinyl monomers. Illustrative of the N-vinyl lactams that are employed in this invention are: N-vinyl-2-pyrrolidinone, N-(1-methyl vinyl) pyrrolidinone, N-vinyl-2-piperidone and N-vinyl-2-caprolactam which may be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone and N-vinyl-6-methyl piperidone. Illustrative of the other heterocyclic N-vinyl monomers used in preparing the polymers of this invention are: N-vinyl imidazole, N-vinyl succinimide, N-vinyl diglycolylimide, N-vinyl glutarimide, N-vinyl-3-morpholinone and N-vinyl-5-methyl-3-morpholinone. The lactams may be effectively employed alone or in admixture with other lactam monomers to give hydrogels having the foregoing desirable characteristics. The preferred monomer is N-vinyl-2-pyrrolidinone.

Most usually, the N-vinyl lactam monomer(s) will be used in conjunction with one or more hydrophobic and/or hydrophilic comonomers. When used in conjunction with a comonomer, the N-vinyl lactam will constitute at least 50% of the copolymer and more preferably from 70% to 90% by weight of the total monomers employed. One or more hydrophobic comonomers may constitute the total copolymer admixed with the N-vinyl lactam. One or more hydrophilic comonomers may also constitute the total comonomer admixed with the N-vinyl lactam. Furthermore, the ratio of hydrophobic comonomer to hydrophilic comonomer employed in preparing the N-vinyl lactam copolymers of this invention may be varied as desired to obtain the particular combination of polymer properties desired for the particular application. Lower amounts of the N-vinyl lactam or other hydrophilic comonomers will result in lower amount of water content and consequently lower oxygen permeability of the polymer and greater mechanical strength. The preferred amount of N-vinyl lactam in the polymer composition is 70 to 90 percent by weight to achieve a high water content of 70 to 90 percent and preferably 70 percent or more. The percent water is calculated as follows:

$$\text{Percent Water} = \frac{\text{Wet Weight} - \text{Dry Weight}}{\text{Wet Weight}} \times 100$$

Suitable hydrophobic comonomers for the N-vinyl lactam monomers described above include acrylates, methacrylates, itaconates, fumarates, maleates and crotonates wherein the esterified group has from 1 to 30 carbon atoms. The esterified group can be a substituted or unsubstituted alkyl, cycloalkyl, hydroxyalkyl, hydroxyalkoxyalkyl, polycyclic or aryl. Exemplary of the esterified aliphatic alcohols, both straight or branched chain, are alkyls such as butyl, dodecyl, ethyl, 3-ethoxypropyl, heptyl, hexadecyl, hydroxyethyl, hydroxypropyl, isopropyl, methyl, 3,3-dimethylbutyl, lauryl, octadecyl and stearyl. Suitable cycloalkyl groups include cyclohexyl, tertiarybutyl-cyclohexyl, menthyl, isopropylcyclopentyl, tertiary-butyl-pentyl and methylisopentyl. Suitable polycyclic groups include isobornyl, adamantyl and isopinocamphyl. Exemplary ethers include ethers of ethylene glycol, such as di-, tri-, tetra- or polyethylene glycol. Illustrative of suitable aryl groups are phenyl, phenylethyl, naphthyl, benzyl, biphenyl, 4-butoxycarbonylphenyl, m-tolyl and 4-methoxycarbonylphenyl.

Illustrative of suitable hydrophilic comonomers are the mono-, di-, tri-, tetra- and poly-ethylene glycol monoacrylates or methacrylates or itaconates as well as the acids per se. Useful amides of the foregoing acids include acryl, methacryl, N-mono- or di-substituted diacetone acrylamide. Also useful are the amines of the foregoing acids such as mono- or di-alkylamino substituents.

It is within the scope of this invention that hydrophilic comonomers as well as hydrophobic comonomers disclosed by the prior art can be advantageously used within the scope of this invention.

The advantageous compositions of this invention are obtained by the incorporation therein of a resonance free di(alkene tertiary amine) cyclic compound as a crosslinker. The crosslinkers can be simplistically visualized as of the formula $CH_2:CG(CH_2)_xN\sim J\sim N(CH_2)_xCG:CH_2$ wherein x is 0 or 1, G is hydrogen or methyl and the J group is the balance of a structure forming a cyclic dialkene urea, a dialkene hydrazide, dialkene amide, dialkene hydantoin, dialkene hydrouracil or a dialkene 2,2'-bisimidazolin. The alkene group in the cyclic compounds of this invention is either vinyl (when x is 0) or allyl (when x is 1) and G is hydrogen or alpha methyl vinyl or alpha methyl allyl when G is methyl. Illustrative of cyclic dialkene ureas useful in this invention are N,N'-divinyl ethylene urea (also known as N,N'-divinyl imidazolid-2-one) having the formula

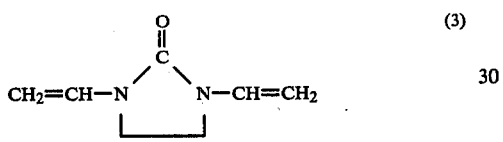

the corresponding N,N'-diallyl ethylene urea and N,N'-di(alpha methyl vinyl) ethylene urea, N,N'-diallyl propylene urea and the corresponding N,N'-di(alpha methyl allyl) propylene urea and N,N'-divinyl propylene urea (also known as N,N'-divinyl hexahydropyrimidine-2-one) having the formula

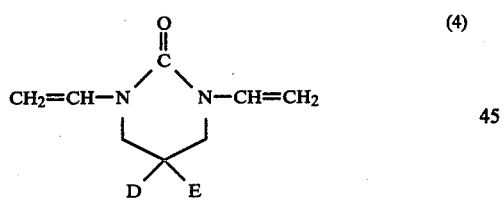

wherein D and E are each independently selected from the group consisting of hydrogen or alkyl of 1 to 12 carbon atoms and preferably 1 to 6 carbon atoms. In the foregoing formula (4) when both D and E are hydrogen, the compound is the forementioned N,N'-divinylpropylene urea. Still other useful cyclic di(alkene ureas) the compounds such as those having the structural formulas shown in formulas (5), (6) and (7) below wherein x in each case is 0 or 1 and G is hydrogen or methyl,

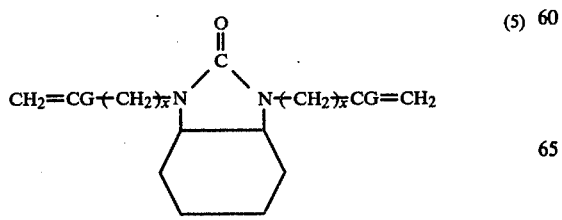

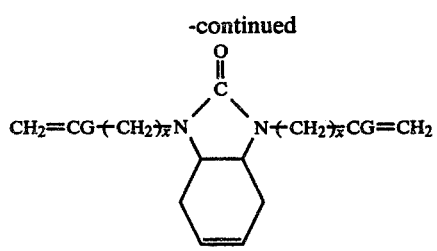

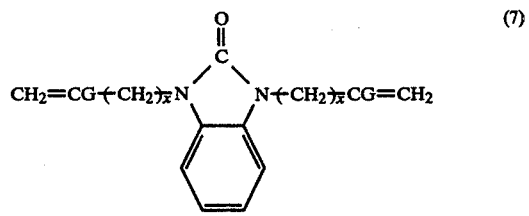

Illustrative of the di(alkene amides) useful as crosslinking agents in the present invention are compounds having chemical structures represented by the formulas (8) and (9) below,

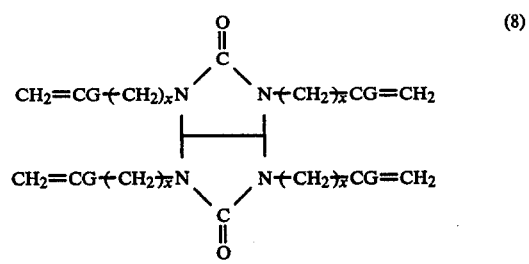

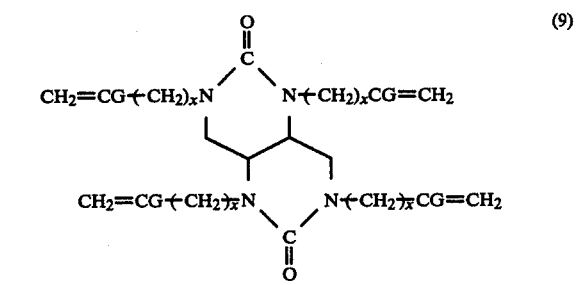

Illustrative of the di(alkene) hydrazides useful as crosslinking agents in the present invention are compounds having chemical structures illustrated by formulas (10) and (11) below,

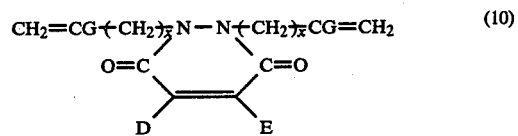

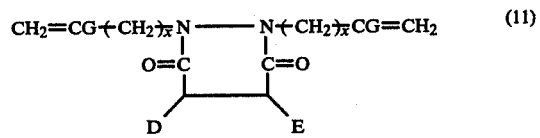

The di(alkene) hydantoins useful as crosslinking agents in this invention have the general formula,

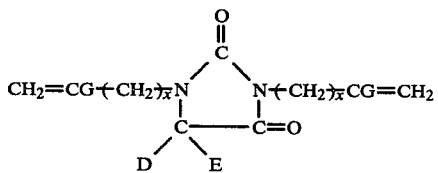

Illustrative of the di(alkene) hydrouracils suitable as a crosslinking agent of this invention are those shown in formulas (13) and (14) below,

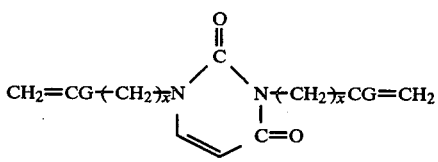

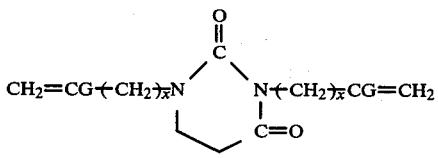

Finally, illustrative of the di(alkene) 2,2'-bis-imidazolin useful as a crosslinking agent in the present invention is 1,1'-diallyl-2,2'-bis-imidazolin and the corresponding 1,1'-divinyl-2,2'-bis-imidazolin which has the formula

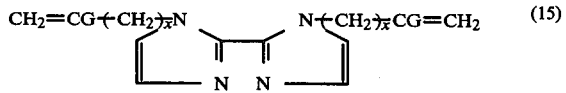

In Formulas 4, 10, 11, and 12 above, D is hydrogen or alkyl of $C_1-C_{12}$, preferably $C_1-C_6$; E is hydrogen or alkyl of $C_1-C_{12}$, preferably $C_1-C_6$. In Formulas 5 through 15 inclusive above, G is hydrogen or methyl and x is 0 or 1.

The foregoing di(alkene) tertiary amine) compounds can be used either singularly or in combination with one another in obtaining the desired crosslinking structure of the polymers of this invention. The di(alkene tertiary amine) compound is present in an amount from 0.01 to 10 weight percent and preferably from 0.1 to about 3.0 percent. In order to further modify the polymers of this invention and to obtain some enhancement of a particular feature up to 50 mole percent but preferably no more than 20 mole percent of the di(alkene) cyclic compound employed in this invention may be substituted by well-known and widely used crosslinking agents in the prior art. When judged on an overall property basis, polymers having from 20 to 50 mole percent substitution of crosslinking agent result in contact lenses which are less satisfactory. Suitable prior art crosslinking agents include mono-, di-, tri-, tetra-, poly-, ethylene glycol diacrylates or dimethacrylates, vinyl or allyl acrylates or methacrylates, divinylbenzene, allyl esters such as diallyldiglycol dicarbonate, diallyl maleate, diallyl fumarate, diallyl itaconate, vinyl esters such as divinyl oxalate, divinyl malonate, diallyl succinate, and the like, triallyl isocyanurate, the dimethacrylates or diacrylates of bis-phenol A or ethoxylated bis-phenol A and hexamethylene bisacrylamide or hexamethylene bismethacrylamide.

The N-vinyl lactam monomers of this invention when mixed with the resonance free di(alkene tertiary amine) cyclic compound crosslinking agent with or without optional additional crosslinking agents and hydrophobic or hydrophilic monomers are generally clear, colorless liquids of varying viscosity. These monomer mixtures can be readily cured to cast shapes by conventional methods such as free radical initiation.

The free radical type initiators suitable for this invention include peroxides, azo compounds, UV initiation, oxidation-reduction systems and similar initiators described in the literature. Illustrative of free radical initiators which can be employed are bis(isopropyl) peroxy dicarbonate, 2,2'-azobis[isobutyronitrile], acetyl peroxide, benzoin methyl ether, lauroyl peroxide, decanoyl peroxide, benzoyl peroxide, 2,2'-azobis[2,4-dimethylvaleronitrile], tertiarybutyl peroctoate, phthalic peroxide, cumene hydroperoxide, diethoxyacetophenone, tertiarybutyl peroxypivalate and the like.

As is well known in the contact lens art, water soluble diluents may be used with the foregoing polymers to modify the physical properties of these polymers. More particularly, the diluents may be advantageous in improving machinability and swell characteristics of the polymer. Typically, the amount of diluent will be less than 50 weight percent of the total monomers employed and preferably not more than 30 weight percent. In a particular polymer system, the limiting amount of diluent is the solubility of the diluent in the monomer system. Thus, there should be no phase separation between diluent and starting monomer mixture. Additionally, excessive amounts of diluent will result in collapse of the cell structure of the finished biomedical devices when the device is hydrated, i.e., replacement of diluent by water. The maximum amount of diluent is readily ascertained by swelling the diluent free polymer in the proposed diluent and measuring the degree of swell. Comparable results are obtained when using solvent soluble diluents wherein the solvent does not affect the lens polymer. These solvents include ketones, e.g., methyl ethyl ketone and isopropyl alcohol. Suitable diluents include ethylene glycol, glycerine, liquid polyethylene glycols, butanol, butanol/water mixtures, ethylene oxide/propylene oxide block copolymers having a molecular weight from 1,000 to 5,000, low molecular weight, e.g., 500 to 10,000, linear poly(vinyl pyrrolidinone), low molecular weight linear poly(hydroxyethyl methacrylate), glycol esters of lactic acid, formamide, dimethyl formamide, methyl ethyl ketone, dimethyl sulfoxide and the like. In the finished biomedical device, it will be necessary to replace any diluent with an aqueous solution. The contact lens should, of course, contain a physiological saline solution as the aqueous medium.

The polymers of this invention can be formed into medical surgical devices and contact lenses by methods well known in the prior art. By way of example, mixture of the desired N-vinyl lactam, free radical type initiator, the di(alkene tertiary amine) cyclic compound crosslinking agent and any optional crosslinker or monomer described above is purged with an inert gas such as nitrogen or carbon dioxide and filled into polypropylene tubes having dimensions of 18 mm×300 mm. The polymerization is then carried out by gradually heating from 30° C. to 110° C. in a step fashion over a span of several days. In a typical schedule the tubes are placed in a water bath from 30° C. to 50° C. for two to three days followed by two days at 60° C. The rod is then removed from the mold and post-cured at 110° C. for a period of up to about four hours. The fully cured rods are then cut into cylinders, optionally then annealed at temperatures up to 150° C. and machined to form contact lenses as desired. Other conventional methods such as compression molding as disclosed in U.S. Pat. Nos. 4,084,459 and 4,197,266 or spincasting process as described in U.S. Pat. Nos. 3,408,429 and 3,496,254 can be employed to prepare useful objects of this invention.

The contact lenses made from the polymer of the instant invention are oxygen permeable. A critical oxygen tension and flux under a lens should be about 10 mmHg and 2 ml/(cm²hr.) respectively below which corneal swelling occurs, see Polse and Decker, *Investigative Ophthalmology and Visual Science*, vol. 18, p 188, 1979. In order to meet these requirements, the lens material must have adequate oxygen permeability. These more preferred contact lenses have an oxygen permeability of at least about $24 \times 10^{-11} cm^3 cm/(sec.cm^2 mmHg)$, are hydrolytically stable, biologically inert and transparent. The most preferred contact lenses have an oxygen permeability of at least $30 \times 10^{-11}$. In comparison, the well-known contact lens polymer poly(hydroxyethyl methacrylate) has an oxygen permeability value of about one-third of the polymers of this invention.

Additionally, these lenses are hydrolytically stable meaning that when the contact lenses are placed into an aqueous solution, e.g., on the eye, or during the disinfecting step, i.e., water plus heat, the lenses will not change in chemical composition, i.e., hydrolyze. On heating in boiling water for 120 hours, the typical polymer of this invention experiences a water content loss of three percent or less. The most preferred lenses/polymers of this invention have a stable, i.e., less than one percent change, water content.

Thus, the polymers and copolymers disclosed herein can be boiled and/or autoclaved in water without being damaged whereby sterilization may be achieved. An article formed from the disclosed polymers and copolymers may be used in surgery where an article compatible with living tissue or with the mucous membranes may be used.

The polymers and copolymers of this invention being soft yet resilient and hard to tear are well suited for use in biomedical devices, including contact lenses. It is well known that the wearer of soft contact lenses will have an unavoidable amount of handling of the lenses. Part of the cleaning and rinsing procedure is to rub each lens and tearing has been a concern in prior art lenses. The polymers and copolymers of the present invention have a tear initiation strength (ASTM D-1938) of at least 3 g/mm of thickness and preferably 4 g/mm or more.

These polymers can also be used in preparing medical surgical devices, e.g., heart valves, vessel substitutes, intrauterine devices, membranes and other films, dialyzer diaphragms, catheters, mouth guards, denture liners and other such devices as disclosed in Shephard U.S. Pat. Nos. 3,618,231 and 3,520,949. The instant polymers can be used to modify collagen to make blood vessels, urinary bladders and other such devices as disclosed in Kliment, U.S. Pat. No. 3,563,925. Also, these polymers can be used to make catheters as disclosed in Shephard U.S. Pat. No. 3,566,874. These polymers can be used as semipermeable sheets for dialysis, artificial dentures and all of such disclosures as set forth in Stoy, U.S. Pat. No. 3,607,848. The instant polymers can be used in making breathable leather and other materials as disclosed in Shephard, U.S. Pat. No. 3,660,218.

The terms "shaped article for use in biomedical applications" or "biomedical devices" mean the materials disclosed herein have physiochemical properties rendering them suitable for prolonged contact with living tissue, blood and the mucous membranes. These properties are required for biomedical shaped articles such as surgical implants, blood dialysis devices, blood vessels, artificial ureters, artificial breast tissue and membranes intended to come in contact with body fluid outside of the body, e.g., membranes for kidney dialysis and heart-/lung machines and the like. It is known that blood, for example, is rapidly damaged in contact with artificial surfaces. The design of a synthetic surface which is antithrombogenic and nonhemolytic to blood is necessary for prostheses and devices used with blood. The polymers and copolymers are compatible with living tissue.

The following examples are illustrative only and should not be construed as limiting the invention. All parts and percents referred to herein are on a weight basis. Temperature is expressed in degrees Celsius unless otherwise specified.

EXAMPLE I

To a mixture containing 80 g of N-vinyl pyrrolidinone, 15 g of methyl methacrylate, 5 g cyclohexyl methacrylate (herein after referred to as CHM) monomers and 0.2 g of 2,2'-azobis(isobutyronitrile) polymerization initiator is admixed the crosslinking agent as indicated in Table I below. The solution is purged with nitrogen for 10 minutes and then poured into polypropylene tubes having a diameter of 18 mm and a length of 300 mm. The tubes are closed and then immersed in a constant temperature bath and heated to 30° to 35° C. for 72 hours, then the temperature is raised to and maintained at 42°–47° C. for 48 hours and then a final heating period of 60° C. for one hour. The resulting rod is removed from the tube and post-cured for two hours at 110° C. Cylinders are cut from the rod. From the cylinders, lenses or flat disks are machined. The water content of the polymer is determined by change in weight after boiling the flat disk in water for (1) a half-hour and (2) 120 hours. This test establishes the stability of the polymer.

For convenience, hereinafter the divinyl ethylene urea crosslinker of this invention will be referred to as DVEU and the crosslinking agents of the prior art diallyl maleate and ethylene glycol dimethacrylate will be respectively referred to as DAM and EGDMA.

TABLE I

| EFFECT OF CROSSLINKING AGENT | | | |
|---|---|---|---|
| | | Water Content After Extraction at 100° C., % | |
| Type | Amount, g | 0.5 hr. | 120 hrs. |
| DVEU | 0.3 | 81.3 | 80.8 |
| DVEU | 0.6 | 78.7 | 78.5 |
| DVEU | 1.0 | 77.0 | 76.9 |
| DVEU, 4 mols } EGDMA, 1 mol | 0.3 | 75.0 | 72.0 |
| EGDMA | 0.3 | 77.1 | 63.6 |
| DAM | 0.3 | 73.7 | 66.7 |

From Table I it can be seen that when the cross-linking agent employed is from the prior art (DAM, EDGMA) the water content of the polymer diminishes significantly after 120 hours extraction. This phenomena indicates instability of the polymer and possible polymer structural changes. In contrast, the resonance free di(alkene tertiary amine) cyclic compound crosslinking agenty of this invention, DVEU, crosslinked polymers do not show a significant change in water content for the same test period.

EXAMPLE II

Additional polymeric compositions were prepared following the formulation and procedure of Example I except as noted in conjunction with each of the formulations A through F below. Compositions E and F are comparative formulations using crosslinking agents disclosed in the prior art. The physical properties of the hydrated copolymers are tested and their results compared in Table II below. Unless otherwise stated, the crosslinking agent is 0.3 g of a mixture of DVEU/EGDMA in a mole ratio of 4:1.

Composition A

The hydrophobic comonomer CHM is replaced by an equal amount of tertiarybutylcyclohexyl methacrylate.

Composition B

The hydrophobic comonomer CHM is replaced by an equal amount of isobornyl acrylate.

Composition C

The hydrophobic comonomer CHM is replaced by an equal amount of adamantyl methacrylate.

Composition D

This is the same as Example I.

Composition E

This is a comparative formulation wherein the monomer mixture is the same as that of Example I. However, the crosslinking agent is from the prior art. In this composition, 0.3 g of allyl methacrylate was used as the crosslinking agent.

Composition F

This is a comparative example utilizing the same monomer mixture as in Example I. However, the crosslinking agent is the prior art crosslinking agent diallyl maleate which is present in an amount of 0.3 g.

high initial water content, fail to achieve the very critical tear initiation strength properties of Composition G.

EXAMPLE III

Additional monomeric compositions are prepared and crosslinked following the procedures set out in Example I. In these compositions, the hydrophobic monomer, methyl methacrylate, has been replaced by other hydrophobic and hydrophilic monomers. Each of the prepared compositions is tested for water content as in Example I. The complete formulation of each composition and the water extraction results are tabulated in Table III below. An inspection of Table III below reveals that hydrolytically stable copolymers having a higher water content are obtained even when the methyl methacrylate is completely replaced.

TABLE III

| | HYDROLYTIC STABILITY | | | | | |
|---|---|---|---|---|---|---|
| | A | B | C | D | E | F |
| Composition | | | | | | |
| N—Vinyl Pyrrolidinone - Parts | 80 | 80 | 80 | 80 | 80 | 80 |
| Hydroxyethyl Methacrylate - Parts | 10 | 8 | 10 | 8 | 10 | 8 |
| Isobornyl Acrylate - Parts | 10 | 12 | — | — | — | — |
| Isobornyl Methacrylate - Parts | — | — | 10 | 12 | 10 | 12 |
| DVEU/EGDMA (4:1) - Parts | 0.6 | 0.6 | 0.6 | 0.6 | — | — |
| DVEU - Parts | — | — | — | — | 0.6 | 0.6 |
| Water Content, Extraction at 100° C. | | | | | | |
| After ½ Hour, % | 77.0 | 75.0 | 77.0 | 74.9 | 75.3 | 72.2 |
| After 120 Hours, % | 76.1 | 74.4 | 76.4 | 74.5 | 75.6 | 73.4 |

EXAMPLE IV

Following the procedure of Example I, additional copolymers are prepared and then evaluated for oxygen permeability characteristics. To avoid differences in the

TABLE II

| PHYSICAL PROPERTIES OF COPOLYMERS | | | | | | | |
|---|---|---|---|---|---|---|---|
| | COMPOSITION | | | | | | |
| | THIS INVENTION | | | | PRIOR ART | | |
| | A | B | C | D | E | F | G |
| Tensile Strength, g/mm² (ASTM D-1708) | 84 | 41 | 35 | 26 | 35 | 37 | 46 |
| Modulus of Elasticity, g/mm² (ASTM D-1708) | 45 | 29 | 24 | 23 | 38 | 42 | 57 |
| Elongation, Ultimate, % (ASTM D-1708) | 194 | 231 | 216 | 145 | 152 | 130 | 177 |
| Tear Initiation, g/mm of Thickness (ASTM 1938) | 7.68 | 4.73 | 4.57 | 4.10 | 2.76 | 2.41 | 4.34 |
| Initial Water Content, % | 78.6 | 79.5 | 79.8 | 81.0 | 76.2 | 75.3 | 38 |

Composition G

This composition is poly(hydroxyethyl methacrylate), hereinafter referred to as PHEMA, a well-known polymer used for soft contact lenses. The values given for this compound are typical values taken from the literature for comparison purposes.

Tear strength is a very important property in considering polymeric compositions for soft contact lenses. It is well known that the wearer of soft contact lenses, following approved procedures, will have an unavoidable amount of handling of the lenses each day. The results in Table II below show that the polymers according to this invention (A,B,C,D) have mechanical properties similar to PHEMA (Composition G) except that the initial water content is about double that of Composition G. Compositions E and F, while having interpretation of the oxygen permeability determination, poly(hydroxyethyl methacrylate) hydrogel (PHEMA) was used as a control. The oxygen permeability is expressed as a ratio of the permeability of the copolymer/permeability of PHEMA. A typical oxygen permeability value for PHEMA hydrogel: $8.0 \times 10^{-11}$ cm³cm/(sec.cm²mmHg). The oxygen permeability measurements were made using a flat polarographic sensor. The method used was basically that described by Refojo, M., Holly, F. and Leong, F-L., *Contact and Intraocular Lens Medical Journal*, Vol. 3, Issue 4, p 27, (1977). The determinations are carried out on samples having a thickness of about 0.3 mm. The values are corrected for sample thickness. The results are tabulated in Table IV below. As seen from the results, oxygen permeability of the polymer of this invention with DVEU crosslinking agent is higher than the copolymers utilizing the prior art crosslinking agents, allyl methacrylate or DAM.

drated and then extracted in boiling saline solution for one hour. The lenses are placed on Cynomolgus mon-

TABLE IV

| OXYGEN PERMEABILITY | | | | | | | | | | | | | |
|---|---|---|---|---|---|---|---|---|---|---|---|---|
| COMPOSITION | A | B | C | D | E | F | G | H | I | J | K | L | M |
| N—Vinyl Pyrrolidinone, Parts | 80 | 80 | 80 | 80 | 80 | 80 | 80 | 80 | 80 | 80 | 80 | 80 | 80 |
| Comonomer, Parts | | | | | | | | | | | | | |
| Adamantyl Methacrylate | — | — | 5 | — | — | — | — | — | 5 | — | — | — | — |
| t-Butyl Cyclohexyl Methacrylate | — | — | — | — | — | — | — | — | — | — | — | — | — |
| Cyclohexyl Methacrylate | 5 | 5 | — | 5 | 5 | 5 | 5 | 5 | — | — | — | — | — |
| 2-Hydroxyethyl Methacrylate | — | — | — | — | — | — | — | — | — | — | — | — | — |
| Isobornyl Methacrylate | — | — | — | — | — | — | — | — | — | — | — | — | 5 |
| Isobornyl Acrylate | — | — | — | — | — | — | — | — | — | — | 5 | 10 | — |
| Methyl Methacrylate | 15 | 15 | 15 | 15 | 15 | 15 | 15 | 15 | 15 | 15 | 15 | 15 | 15 |
| Crosslinking Agent, Parts | | | | | | | | | | | | | |
| (a) Prior Art | | | | | | | | | | | | | |
| Allyl Methacrylate | — | 0.3 | — | — | — | — | — | — | — | — | — | — | — |
| DAM | 0.3 | — | 0.3 | — | — | — | — | — | — | — | — | — | — |
| Ethylene Glycol Dimethacrylate | | | | | | | | | | | | | |
| (b) This Invention | | | | | | | | | | | | | |
| DVEU | — | — | — | — | — | — | — | 0.3 | — | — | — | — | 0.3 |
| DVEU/EGDMA (4:1) | — | — | — | 0.3 | 0.6 | 1.0 | 2.0 | — | 0.3 | 0.3 | 0.3 | 0.3 | — |
| Oxygen Permeability × P (HEMA) | 2.6 | 2.6 | 3.0 | 5.3 | 4.7 | 4.2 | 3.7 | 4.7 | 3.3 | 4.1 | 3.9 | 4.3 | 3.8 |

| COMPOSITION | N | O | P | Q | R | S | T | U | V | W | X | Y |
|---|---|---|---|---|---|---|---|---|---|---|---|---|
| N—Vinyl Pyrrolidinone, Parts | 80 | 80 | 80 | 80 | 80 | 80 | 80 | 80 | 80 | 80 | 80 | 80 |
| Comonomer Parts | | | | | | | | | | | | |
| Adamantyl Methacrylate | — | — | — | — | — | — | — | — | — | — | — | — |
| t-Butyl Cyclohexyl Methacrylate | — | — | 5 | — | — | — | 13 | — | — | — | — | — |
| Cyclohexyl Methacrylate | — | — | — | — | — | — | — | — | — | — | — | — |
| 2-Hydroxyethyl Methacrylate | — | — | — | 15 | 10 | 5 | 15 | 10 | 5 | 10 | 8 | 8 |
| Isobornyl Methacrylate | 5 | 5 | — | — | — | — | 5 | 10 | 15 | 10 | 12 | 12 |
| Isobornyl Acrylate | — | — | — | 5 | 10 | 15 | — | — | — | — | — | — |
| Methyl Methacrylate | 15 | 15 | — | — | — | — | — | — | — | — | — | — |
| Crosslinking Agent, Parts | | | | | | | | | | | | |
| (a) Prior Art | | | | | | | | | | | | |
| Allyl Methacrylate | — | — | — | — | — | — | — | — | — | — | — | — |
| DAM | — | — | — | — | — | — | — | — | — | — | — | — |
| Ethylene Glycol Dimethacrylate | | | | | | | | | | | | |
| (b) This Invention | | | | | | | | | | | | |
| DVEU | 0.6 | 1.0 | — | — | — | — | — | — | — | 0.6 | 0.6 | 0.3 |
| DVEU/EGDMA (4:1) | — | — | 0.3 | 0.3 | 0.3 | 0.3 | 0.3 | 0.3 | 0.3 | — | — | — |
| Oxygen Permeability × P (HEMA) | 3.3 | 3.5 | 4.8 | 4.9 | 5.2 | 4.8 | 4.6 | 4.8 | 3.7 | 3.4 | 3.5 | 5.5 |

EXAMPLE V

Three copolymer compositions are prepared and fabricated into rods following the procedures of Example I. Disks (0.5 mm thick) are cut from the rods thus prepared and are used for cytoxicity testing. The first copolymer is based on 80 parts of N-vinyl pyrrolidinone, 15 parts of methyl methacrylate, 5 parts of cyclohexylmethacrylate and 1 part of DVEU. The second copolymer is formulated from 80 parts of N-vinyl pyrrolidinone, 8 parts of hydroxyethyl methacrylate, 12 parts of isobornyl methacrylate and 0.3 parts of DVEU. The third copolymer composition is based on 80 parts of N-vinyl pyrrolidinone, 15 parts of methyl methacrylate, 5 parts isobornyl methacrylate and 1 part of DVEU. Cytoxicity is determined by using the agar overlay method described by W. L. Guess, S. A. Rosenbluth, B. Schmidt and J. Autian in the Journal of Pharmaceutical Science, vol. 54, p 1545 (1965). In this method L 929 mouse fibroblast cells are used. The three copolymers are non-cytoxic.

EXAMPLE VI

Portions of the copolymers prepared in Example V are made into contact lenses using the conventional lathing and polishing techniques. The lenses are hydrated and then extracted in boiling saline solution for one hour. The lenses are placed on Cynomolgus monkey eyes and examined at intervals between 4 and 15 hours for a total period of 43 hours. Biomicroscopic examination of the eyes is carried out in white light and with a cobalt blue filter and fluoresein installation. After 43 hours of wear by the monkeys, with no corneal insult and no adverse signs or symptoms being observed, the lenses are removed and the test discontinued.

EXAMPLE VII

Following the procedure of Example I, a copolymer is prepared from a monomer mixture containing 90 parts of N-vinyl imidazole, 10 parts of t-butyl cyclohexyl methacrylate, 1 parts of 1,1'-divinyl-2,2'-bisimidazoline and 0.2 parts of 2,2'-azobis(isobutyronitrile). The resultant optically clear rod is lathe cut into buttons from which suitable contact lenses are fabricated.

EXAMPLE VIII

A series of homopolymers are prepared from redistilled N-vinyl pyrrolidinone in which the crosslinking agent is DVEU. The polymerization is initiated by the addition of 0.18 parts of 2,2'-azobis(isobutyronitrile). The solution is cast between glass plates separated by a Teflon ® (DuPont trademark) perfluoro polymer gasket of 0.3 mm thickness. The film is cured for 15 hours at 60° C., then one hour at 80° C. and finally one hour at 100° C. In each insance, clear homogeneous films are obtained. The resulting films are evaluated for initial water content, the results are summarized in Table V below.

TABLE V

| SAMPLE | PARTS OF DVEU | INITIAL WATER CONTENT, % |
|---|---|---|
| A | 0.3 | 92.4 |
| B | 0.6 | 88.6 |
| C | 1.0 | 85.9 |
| D | 2.0 | 81.5 |

EXAMPLE IX

A casting solution is prepared by mixing together 100 parts of N-vinyl-2-caprolactam, 1 part of N,N'-divinyl propylene urea and 0.2 parts of 2,2'-azobis(isobutyronitrile). A clear homogeneous film suitable for optical purposes is prepared when the solution is cast and cured according to the procedure of Example VIII.

EXAMPLE X

A casting solution is prepared by mixing together 100 parts of N-vinyl-3-morpholinone, 1 part of N,N'-divinyl-2,2-dimethyl propylene urea, and 2 parts of diethoxyacetophenone. The mixed, degassed solution is placed in a suitable contact lens spincasting mold. It is spincast with ultraviolet radiation for one-half hour to obtain the desired lens. The lens is optically clear, oxygen permeable, flexible and strong.

EXAMPLE XI

A casting solution is prepared by mixing together 80 parts of N-vinyl glutarimide, 10 parts of lauryl methacrylate, 10 parts diethyleneglycol monoacrylate, 1 part of 1,1'-diallyl-2,2'-bis-imidazolin and 2 parts of diethoxy acetophenone. Following the procedure of Example X, useful contact lenses are obtained by the spincasting method.

EXAMPLE XII

Example VII is repeated except that 15 parts of ethylene glycol is added to the monomer mixture. After fabrication of contact lenses from the buttons, the lenses are soaked in physiological saline to remove the ethylene glycol.

EXAMPLE XIII

A series of polymers was prepared in which only the mole ratio of DVEU to EDGMA is varied. Each polymer is based on 80 g of N-vinyl pyrrolidinone, 15 g of hydroxyethyl methacrylate, 5 g of isobornyl methacrylate, 0.3 g of DVEU/EDGMA and 0.18 g of 2,2'-azobis-(isobutyronitrile). The polymers are polymerized following the procedure of Example I. The water content of each polymer is then determined. The results are tabulated in Table VI below.

TABLE VI

| SAMPLE | MOLES DVEU | MOLES EDGMA | INITIAL WATER CONTENT, % |
|---|---|---|---|
| A | 1 | 1 | 83.4 |
| B | 4 | 1 | 82.9 |
| C | 6 | 1 | 82.9 |
| D | 8 | 1 | 82.6 |
| E | 10 | 1 | 81.6 |

Sample A, while having the slightly higher water content, is not deemed the polymer of choice because of its other physical properties, e.g., significantly higher extractibles.

The preceding examples and methods have been described in the foregoing specification for the purpose of illustration and not limitation. Other modifications ad ramifications will naturally suggest themselves to those skilled in the art based on the disclosure. These are intended to be comprehended as within the scope of this invention.

The embodiments of the invention in which an exclusive property or privilege is claimed are defined as follows:

1. As a new article of manufacture, a contact lens formed from a hydrophilic polymer formed by polymerizing (a) (1) one or more N-vinyl lactams and/or heterocyclic N-vinyl monomers, said N-vinyl lactams being selected from the group consisting of N-vinyl-2-pyrrolidinone, N-(1-methyl) vinyl pyrrolidinone, N-vinyl-2-piperidone and N-vinyl-2-caprolactam which may be substituted in the lactam ring by one or more lower alkyl groups, said heterocyclic N-vinyl monomers being selected from the group consisting of N-vinyl imidazole, N-vinyl succinimide, N-vinyl diglycolylimide, N-vinyl glutarimide, N-vinyl-3-morpholinone and N-vinyl-5-methyl-3-morpholinone, and (2) from zero to 50 weight percent of the total monomer present is at least one hydrophobic monomer or hydrophilic monomer other than N-vinyl lactam and/or heterocyclic N-vinyl monomer, said hydrophobic monomer(s) being selected from the group consisting of acrylates, methacrylates, itaconates, fumarates, maleates and crotonates wherein the esterified group has from 1 to 30 carbon atoms, said hydrophilic monomer(s) being selected from the group consisting of hydroxyesters, free acids, amides and amines of acrylates, methacrylates and itaconates, and (b) a resonance free di(alkene tertiary amine) cyclic compound crosslinking agent alone or in admixture with a crosslinking agent of another chemical structure in which case said cyclic compound is at least 50 mole percent of said mixture, said cyclic compound having the formula $CH_2:CG(CH_2)_xN \sim J \sim N(CH_2)_xCH:CH_2$ wherein x is 0 or 1, G is hydrogen or methyl and J is the balance of structure forming cyclic dialkene urea, said agent being present in an amount from 0.01 to 10 weight percent of the total monomer of (A) (1) and (A) (2) present to form a crosslinked 3-dimensional polymeric network, said polymer having an oxygen permeability of at least $24 \times 10^{-11}$ cm$^2$cm/(sec.cm$^2$mmHg) and a tear initiation strength of at least 3 g/mm of thickness.

2. The article according to claim 1 wherein said polymer has a water absorption content from 60% to 90%.

3. The article according to claim 2 wherein the polymer has a water absorption content of at least 70%.

4. The article according to claim 1 wherein the article is hydrolytically stable, the polymer has no more than a one percent change in water absorption content after heating in boiling water for 120 hours.

5. The article according to claim 1 wherein the resonance free di(alkene tertiary amine) cyclic compound is selected from the group consisting of cyclic dialkene urea, dialkene amides, dialkene hydrazides, dialkene hydantoins, dialkene hydrouracils, dialkene 2,2'-bis-imidazolin and mixtures thereof, said alkene being either vinyl, alpha methyl vinyl, alpha methyl allyl or allyl.

6. The article according to claim 5 wherein the resonance free di(alkene tertiary amine) cyclic compound is a cyclic divinyl area.

7. The article according to claim 6 wherein the cyclic divinyl urea is divinyl ethylene urea.

8. The article according to claim 5 wherein the cyclic compound is a dialkene 2,2'-bis-imidazolin.

9. The article according to claim 8 wherein the dialkene 2,2'-bis-imidazolin is 1,1'-divinyl-2,2'-bis-imidazolin.

10. The article according to claim 8 wherein the 2,2'-bis-imidazolin is 1,1-diallyl-2,2'-bis-imidazolin.

11. The article according to claim 5 wherein the resonance free di(alkene tertiary amine) cyclic compound is a cyclic allyl urea.

12. The article according to claim 11 wherein the cyclic allyl urea is diallyl ethylene urea.

13. The article according to claim 1 wherein at least 80 mole percent of the crosslinking agent is the resonance free di(alkene tertiary amine) cyclic compound.

14. The article according to claim 1 wherein the crosslinking agent is present in an amount from 0.1 to 3.0 weight percent.

15. The article according to claim 1 wherein the N-vinyl lactam and/or heterocyclic N-vinyl monomer is an N-vinyl lactam.

16. The article according to claim 15 wherein the N-vinyl lactam is N-vinyl-2-pyrrolidinone.

17. The article according to claim 15 wherein the N-vinyl lactam is N-vinyl-2-piperidone.

18. The article according to claim 15 wherein the N-vinyl lactam is N-vinyl-2-caprolactam.

19. The article according to claim 1 wherein the N-vinyl lactam and/or heterocyclic N-vinyl monomer is a heterocyclic N-vinyl monomer.

20. The article according to claim 19 wherein the N-vinyl heterocyclic monomer is N-vinyl imidazole.

21. The article according to claim 1 wherein from 70% to 90% by weight of the total monomers employed is the N-vinyl lactam or a mixture of the N-vinyl lactams and from 10% to 30% by weight is the hydrophobic comonomer, the hydrophilic comonomer or a mixture thereof.

22. The article according to claim 21 wherein the N-vinyl lactam is N-vinyl pyrrolidinone and the hydrophobic monomers are methyl methacrylate and cyclohexyl methacrylate.

23. The article according to claim 21 wherein the N-vinyl lactam is N-vinyl pyrrolidinone and the hydrophobic monomers are methyl methacrylate and either isobornyl acrylate or isobornyl methacrylate.

24. The article according to claim 21 wherein the N-vinyl lactam is N-vinyl pyrrolidinone, the hydrophilic monomer is hydroxyethyl methacrylate and the hydrophobic monomer is either isobornyl acrylate or isobornyl methacrylate.

25. The article according to claim 21 wherein the N-vinyl lactam is N-vinyl pyrrolidinone, the hydrophilic monomer is hydroxyethyl methacrylate and the hydrophobic monomer is methyl methacrylate.

26. A process for preparing the article of claim 1 comprising (a) admixing together the monomer and crosslinking agent with a free radical initiator, (b) charging the mixture to a mold and (c) activating and maintaining the activation of the free radical initiator until the desired degree of crosslinking has been obtained.

27. The process of claim 26 wherein a water soluble or solvent soluble diluent is admixed with the monomer and crosslinking agent and after the article has been formed removing the diluent by hydrating the article.

* * * * *